United States Patent
Davis

(10) Patent No.: US 7,879,086 B2
(45) Date of Patent: Feb. 1, 2011

(54) MEDICAL DEVICE HAVING A COATING COMPRISING AN ADHESION PROMOTER

(75) Inventor: Liza J Davis, St. Michael, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 265 days.

(21) Appl. No.: 11/409,468

(22) Filed: Apr. 20, 2006

(65) Prior Publication Data

US 2007/0250159 A1 Oct. 25, 2007

(51) Int. Cl.
A61F 2/06 (2006.01)
(52) U.S. Cl. .............. 623/1.46; 623/1.44; 623/1.42
(58) Field of Classification Search ........... 623/1.42, 623/1.44, 1.46, 1.43
See application file for complete search history.

(56) References Cited

U.S. PATENT DOCUMENTS

| | | | |
|---|---|---|---|
| 4,655,771 A | 4/1987 | Wallsten | |
| 4,954,126 A | 9/1990 | Wallstén | |
| 5,061,275 A | 10/1991 | Wallstén et al. | |
| 5,449,373 A | 9/1995 | Pinchasik et al. | |
| 6,099,562 A | 8/2000 | Ding et al. | |
| 6,790,228 B2 * | 9/2004 | Hossainy et al. | 623/1.46 |
| 6,942,693 B2 | 9/2005 | Chouinard et al. | |
| 2003/0125800 A1 * | 7/2003 | Shulze et al. | 623/1.15 |
| 2004/0034337 A1 * | 2/2004 | Boulais et al. | 604/890.1 |
| 2004/0059409 A1 | 3/2004 | Stenzel | |
| 2004/0086542 A1 * | 5/2004 | Hossainy et al. | 424/423 |
| 2004/0225345 A1 * | 11/2004 | Fischell et al. | 623/1.11 |
| 2004/0230298 A1 * | 11/2004 | Udipi et al. | 623/1.42 |
| 2004/0236416 A1 * | 11/2004 | Falotico | 623/1.42 |
| 2004/0260318 A1 * | 12/2004 | Hunter et al. | 606/153 |
| 2005/0228477 A1 * | 10/2005 | Grainger et al. | 623/1.11 |
| 2006/0241742 A1 * | 10/2006 | Harder et al. | 623/1.42 |
| 2007/0110888 A1 * | 5/2007 | Radhakrishnan et al. | 427/2.1 |

FOREIGN PATENT DOCUMENTS

| | | |
|---|---|---|
| WO | WO 94/16646 A1 | 8/1994 |
| WO | WO 2004/037443 A1 | 5/2004 |
| WO | WO 2005/000164 A1 | 1/2005 |
| WO | WO 2005/007035 A1 | 1/2005 |
| WO | WO 2006/052575 A2 | 5/2006 |

OTHER PUBLICATIONS

Kraton™ FG1901X Polymer.

* cited by examiner

Primary Examiner—Corrine M McDermott
Assistant Examiner—Rebecca Straszheim
(74) Attorney, Agent, or Firm—Mayer & Williams; David B. Bonham; Keum J. Park

(57) ABSTRACT

This invention is directed to a coating for a medical device, such as an intravascular stent, in which the coating, which comprises a first coating region comprising an adhesion promoter and a therapeutic agent. The coating can also include a second coating region which is substantially free of the adhesion promoter or any adhesion promoter. The invention is also directed to a method for manufacturing such a coated medical device.

27 Claims, 8 Drawing Sheets

MEDICAL DEVICE HAVING A COATING COMPRISING AN ADHESION PROMOTER

1. FIELD OF THE INVENTION

This invention relates generally to a medical device, such as an intravascular stent, having a coating disposed on at least a portion of the medical device. More particularly, this invention is directed to a coating in which the coating comprises a first coating region comprising an adhesion promoter and a therapeutic agent. The coating can also include a second coating region which is substantially free of the adhesion promoter or any adhesion promoter. The invention is also directed to a method for manufacturing such a coated medical device.

2. BACKGROUND OF THE INVENTION

A variety of medical conditions are treated by introducing an insertable or implantable medical device into the body. In some instances, exposure to a medical device which is implanted or inserted into the body of a patient can cause the body tissue to exhibit adverse physiological reactions. For example, the insertion or implantation of certain catheters or stents can lead to the formation of emboli or clots in blood vessels. Similarly, the implantation of urinary catheters can cause infections, particularly in the urinary tract. Other adverse reactions to medical devices include, without limitation, cell proliferation which can lead to hyperplasia, occlusion of blood vessels, platelet aggregation, rejection of artificial organs, and calcification.

In order to address such adverse effects, medical devices have included therapeutic agents. Such materials can be incorporated into the materials used to make the device. Alternatively, the therapeutic agents can be included in a coating that is applied to a surface of the medical device.

Moreover, medical devices that include a therapeutic agent can be used for direct or local administration of the therapeutic agent to a particular part of the patient's body. For instance, stents having coatings that include a therapeutic agent can be used to treat or prevent restenosis. In some instances, the coating can also include a polymeric material that affects the delivery or release of the therapeutic agent. For example, various types of coated stents in which the coating includes a therapeutic agent have been used for localized delivery of such therapeutic agent to a body lumen. See, e.g., U.S. Pat. No. 6,099,562 to Ding et al. Such direct or local administration may be more preferred than systemic administration of a therapeutic agent. Systemic administration requires larger amounts and/or higher concentrations of the therapeutic agent because of indirect delivery of such agents to the afflicted area. Also, systemic administration may cause side effects which may not be a problem when the therapeutic agent is locally administered.

Given the advantages of medical devices having coatings that include a therapeutic agent, there exists a need for such coated medical devices, particularly medical devices that have a coating comprising a therapeutic agent and a polymer. Of particular interest are medical device coatings that can control the delivery and release kinetics or profile of a therapeutic agent from the coating and that can be fabricated with minimal efforts. For example, improving the controlled release of the therapeutic agent can be achieved by coating the medical device and then damaging the coating by creating holes, slits, etc. in the coating. Such damage to the coating can affect the release of the therapeutic agent by affecting the effective surface area from which the therapeutic agent can be released from the coating. Nevertheless there exists a need for medical device coatings in which the release profile of a therapeutic agent can be controlled or modified.

3. SUMMARY OF THE INVENTION

The present invention provides a coating for medical devices in which the release profile of a therapeutic agent from the coating can be controlled or modified. In particular, the coatings of the present invention include an adhesion promoter that affects the release profile of the therapeutic agent from the coating. In particular, the adhesion promoter enhances the adhesion of a coating composition on a medical device and thereby affects the release profile of the therapeutic agent of the coating composition. In general, the adhesion promoter can reduce the release of the therapeutic coating. Also provided is a medical device coating in which the rate or profile of release of a therapeutic agent from different regions of the medical device can be varied. By using an adhesion promoter, different types of adhesion promoters, or certain different quantities of an adhesion promoter in certain regions of the coating, the therapeutic agent can be selectively released from these certain regions at a rate or profile that is different from the rate or profile of release of the therapeutic agent from other regions of the coating.

In one embodiment, the invention relates to an implantable stent comprising an intravascular sidewall stent structure having openings therein and designed for permanent implantation into a blood vessel of a patient. There is a coating disposed on the stent structure. The coating has a first coating region disposed on a first region of the stent structure, wherein the first coating region comprises a first coating composition comprising a first adhesion promoter and a second coating composition comprising a first therapeutic agent disposed upon the first coating composition. The coating also has a second coating region disposed on a second region of the stent structure, wherein the second coating region comprises a third coating composition comprising a second therapeutic agent, and wherein the third coating composition is substantially free of the adhesion promoter. In some embodiments, the second coating region is free of any adhesion promoter.

In certain embodiments, there can be more than one coating region. The one or more coating regions can be substantially free of any adhesion promoter. In other embodiments, the first adhesion promoter reduces the rate of release of the first therapeutic agent from the first coating region such that the rate of release of the first therapeutic agent from the first coating region is less than the rate of release of the second therapeutic agent from the second coating region. In still other embodiments, the second coating region further comprises a fourth coating composition disposed between the second region of the stent structure and the third coating composition, wherein the fourth coating composition comprises a second adhesion promoter. In certain embodiments, the first and second coating regions conform to the stent structure so as to preserve the openings of the stent structure. In particular embodiments, each of the one or more coating compositions are the same. In other embodiments, each of the one or more coating compositions are different. In some embodiments, the first coating region is contiguous with the second coating region. In other embodiments, each coating composition can comprise one or more layers.

In particular embodiments, the adhesion promoter comprises parylene, copolymers of styrene and ethylene/butylene (e.g. Kraton 1901), iridium oxide or sulfonated styrene isobutylene copolymers. In some embodiments, the adhesion promoter is less than 10 weight percent of the coating composition. In certain embodiments, the one or more therapeutic agents are the same. In other embodiments, the one or more therapeutic agents are different. In particular embodiments, the therapeutic agent is about 0.01 to about 60 weight percent of the coating composition. In certain embodiments, the one and/or more therapeutic agents comprises paclitaxel, rapamycin, everolimus, tacrolimus or pimecrolimus. In other embodiments, the one and/or more therapeutic agents comprises an antibiotic or anti-restenotic agent. In still other embodiments, the one and/or more therapeutic agents comprises a therapeutic agent that inhibits smooth muscle cell proliferation, contraction, migration or hyperactivity.

In preferred embodiments, the one or more coating compositions can comprise a polymer which can be the same polymer. In particular embodiments, the stent structure comprises a metal. In other embodiments, the stent structure is balloon-expandable. In other preferred embodiments, the stent structure comprises two end portions and a middle portion disposed between the two end portions, wherein the first region of the stent structure is an end portion and the second region of the stent structure is the middle portion. In one embodiment, the stent is a bifurcation stent, i.e. a stent intended to treat bifurcated vessels. In an alternative embodiment, the stent is a bifurcation stent wherein the second region of the stent structure is the region that covers the side branch ostium.

In another embodiment, the invention pertains to an implantable medical device, such as a stent. The stent comprises an intravascular sidewall stent structure having openings therein and designed for permanent implantation into a blood vessel of a patient and a coating disposed on the sidewall stent structure. The coating has a first coating region disposed on a first region of the stent structure. The first coating region comprises a first coating composition comprising an adhesion promoter and a second coating composition comprising a therapeutic agent disposed upon the first coating composition. The coating also has a second coating region, which is contiguous with the first coating region, disposed on a second region of the stent structure. The second coating region comprises the second coating composition, and the second coating region is substantially free of any adhesion promoter.

In another embodiment, the medical device is an implantable stent that is an intravascular, metallic, balloon-expandable sidewall stent structure having openings therein and designed for permanent implantation into a blood vessel of a patient. There is a coating disposed on the sidewall stent structure having a first coating region disposed on a first region of the stent structure, wherein the first coating region comprises a first coating composition comprising an adhesion promoter and a second coating composition comprising an anti-restenotic agent disposed upon the first coating composition. There is a second coating region, which is contiguous with the first coating region, disposed on a second region of the stent structure. The second coating region comprises the second coating composition, and the second coating region is substantially free of any adhesion promoter. The first and second coating regions conform to the openings of the sidewall stent structure so as to preserve the openings.

Furthermore, in one embodiment, the medical device of the invention is an implantable stent comprising an intravascular sidewall stent structure having openings therein and designed for permanent implantation into a blood vessel of a patient. There is a coating disposed on the sidewall stent structure having a first coating region disposed on a first region of the stent structure. The first coating region comprises a first coating composition comprising a first adhesion promoter and a first therapeutic agent. The second coating region is disposed on a second region of the stent structure, wherein the second coating region comprises a second coating composition comprising a second adhesion promoter and a second therapeutic agent. The first adhesion promoter reduces the rate of release of the first therapeutic agent from the first coating region such that the rate of release of the first therapeutic agent from the first coating region is less than the rate of release of the second therapeutic agent from the second coating region.

The first and second coating regions conform to the openings of the sidewall stent structure so as to preserve the openings. The first coating region is contiguous with the second coating region. In certain embodiments, the first and second adhesion promoter are the same and in other embodiments they are different. In some embodiments, the weight percent of the adhesion promoter in the first coating composition is different from that of the second coating composition. The therapeutic agents may comprise paclitaxel, rapacamycin, everolimus, tacrolimus, or pimecrolimus. The therapeutic agent may comprise an antibiotic or an anti-restenotic agent. The therapeutic agent may inhibit smooth muscle cell proliferation, contraction, migration, or hyperactivity. The stent structure may comprise two end portions and a middle portion disposed between the two end portions, and wherein the first region of the stent structure is an end portion and the second region of the stent structure is the middle portion. The stent may be a bifurcation stent. In an alternative embodiment, the stent is a bifurcation stent wherein the second region of the stent structure is the region that covers the side branch ostium.

Moreover, in one embodiment, the medical device is an implantable stent comprising an intravascular sidewall stent structure having openings therein and designed for permanent implantation into a blood vessel of a patient. There is also a coating disposed on the sidewall stent structure having a first coating region disposed on a first region of the stent structure, wherein the first coating region comprises a first coating composition comprising a first adhesion promoter, a polymer and an anti-restenotic agent. There is also a second coating region disposed on a second region of the stent structure, wherein the second coating region comprises a second coating composition comprising a second adhesion promoter, the polymer and the anti-restenotic agent. The first adhesion promoter reduces the rate of release of the anti-restenotic agent from the first coating region such that the rate of release of the anti-restenotic agent from the first coating region is less than the rate of release of the anti-restenotic agent from the second coating region.

In another embodiment, the medical device is an implantable stent that comprises an intravascular, metallic, balloon-expandable sidewall stent structure having openings therein and designed for permanent implantation into a blood vessel of a patient. There is a coating disposed on the sidewall stent structure having a first coating region disposed on a first region of the stent structure. The first coating region comprises a first coating composition comprising a first adhesion promoter, a polymer and/or an anti-restenotic agent. There is also a second coating region disposed on a second region of the stent structure, wherein the second coating region comprises a second coating composition comprising a second adhesion promoter, the polymer and/or the anti-restenotic agent. The first adhesion promoter reduces the rate of release of the anti-restenotic agent from the first coating region such that the rate of release of the anti-restenotic agent from the first coating region is less than the rate of release of the anti-restenotic agent from the second coating region. The first and second coating regions conform to the sidewall stent structure so as to preserve the openings therein.

In addition, in another embodiment, the invention is directed to a method for coating an implantable stent comprising a stent having an intravascular sidewall stent structure having openings therein and designed for permanent implantation into a blood vessel of a patient. The first coating region on a first region of the stent structure is formed by disposing a first coating composition comprising a first adhesion promoter on the first region of the stent structure. The second coating composition is formed by disposing a first therapeutic agent onto the first coating composition. A second coating region on a second region of the stent structure is created by disposing a third coating composition comprising a second therapeutic agent onto the second region of the stent structure. The third coating composition is substantially free of the adhesion promoter or free of any adhesion promoter. In some embodiments, the method is claimed where the second coating region is substantially free of any adhesion promoter. In other embodiments, the first adhesion promoter reduces the rate of release of the first therapeutic agent from the first coating region such that the rate of release of the first therapeutic agent from the first coating region is less than the rate of release of the second therapeutic agent from the second coating region. In preferred embodiments, there is a fourth coating composition comprising a second adhesion promoter disposed onto the second region of the stent structure prior to disposing the third composition onto the fourth composition. In alternative embodiments, the first and second coating regions conform to the sidewall stent structure so as to preserve the openings therein. In some embodiments, the second and third coating compositions are the same. In other embodiments, the first coating region is contiguous with the second coating region. In other embodiments, the coating compositions can consist of one or more layers. In certain embodiments, the one or more therapeutic agents are the same. In other certain embodiments, the one or more coating compositions comprise a polymer, which can be the same polymer. In particular embodiments, the stent structure comprises two end portions and a middle portion disposed between the two end portions, wherein the first region of the stent structure is an end portion and the second region of the stent structure is the middle portion. In other particular embodiments, the stent is a bifurcation stent wherein the first region of the stent structure is the region that covers the side branch ostium.

In one embodiment, the method for coating an implantable stent comprises a stent having an intravascular sidewall stent structure having openings therein and designed for permanent implantation into a blood vessel of a patient. A first coating region is formed on a first region of the stent structure by disposing a first coating composition comprising a first adhesion promoter and a first therapeutic agent on the first region of the stent structure.

A second coating region is formed on a second region of the stent structure by disposing a second coating composition comprising a second adhesion promoter and a second therapeutic agent onto the second region of the stent structure. The first adhesion promoter reduces the rate of release of the first therapeutic agent from the first coating region such that the rate of release of the first therapeutic agent from the first coating region is less than the rate of release of the second therapeutic agent from the second coating region. In certain embodiments, the first and second coating regions conform to the sidewall stent structure so as to preserve the openings therein. In other embodiments, the second and third coating compositions are the same. In certain embodiments, the first coating region is contiguous with the second coating region. In particular embodiments, the first and second adhesion promoters are the same. In some embodiments, the weight percent of the adhesion promoter in the first coating composition is different from the weight percent of the adhesion promoter in the second coating composition. In particular embodiments, the first and second therapeutic agents are the same. In certain embodiments, the first and/or second coating composition comprise a polymer. In other embodiments, the stent structure comprises two end portions and a middle portion disposed between the two end portions, and wherein the first region of the stent structure is an end portion and the second region of the stent structure is the middle portion. In various embodiments, the stent is a bifurcation stent wherein the first region of the stent structure is the region that covers the side branch ostium.

4. BRIEF DESCRIPTION OF THE DRAWINGS

5. DETAILED DESCRIPTION

Figure 1:
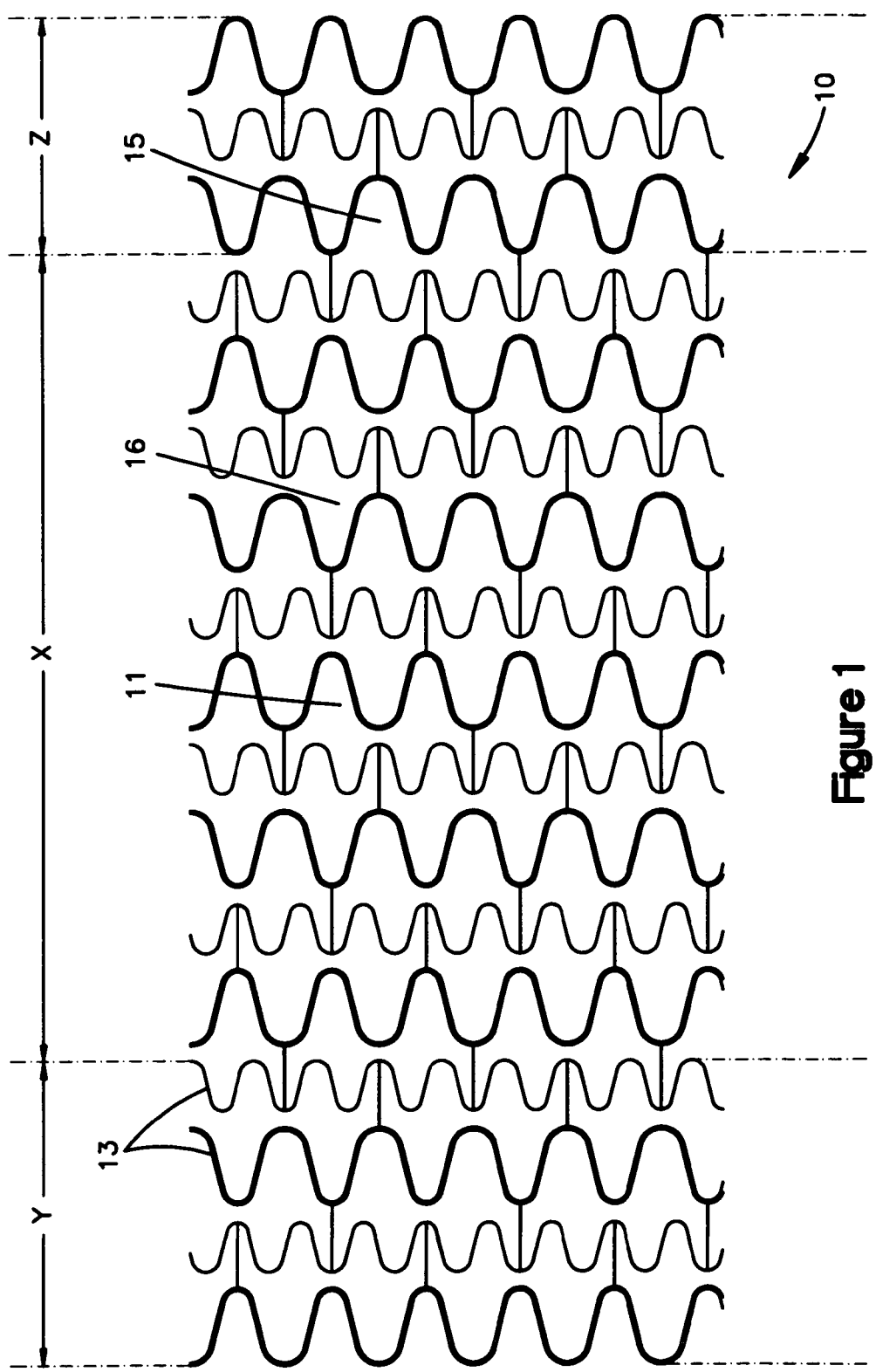
FIG. 1 shows an example of an intravascular stent having a middle portion disposed between two end portions.

The medical devices of the present invention comprise a coating having a first coating region and a second coating region. FIG. 1 shows an example of a medical device that is suitable for use in the present invention. This figure shows an implantable intravascular stent 10 comprising a sidewall 11 which comprises a plurality of struts 13 and at least one opening 15 in the sidewall 11. Generally, the openings 15 are disposed between adjacent struts 13. This embodiment is an example of a stent where the struts and openings of the stent define a sidewall stent structure having openings therein. Also, the sidewall 11 may have a first sidewall surface 16 and an opposing second sidewall surface, which is not shown in FIG. 1. The first sidewall surface 16 can be an outer sidewall surface, which faces the body lumen wall when the stent is implanted, or an inner sidewall surface, which faces away from the body lumen wall. Likewise, the second sidewall surface can be an outer sidewall surface or an inner sidewall surface. The stent 10 comprises a middle portion x and two end portions y and z. Generally, the end portions comprise about 20% or less of the overall length of the stent.

Figure 2:
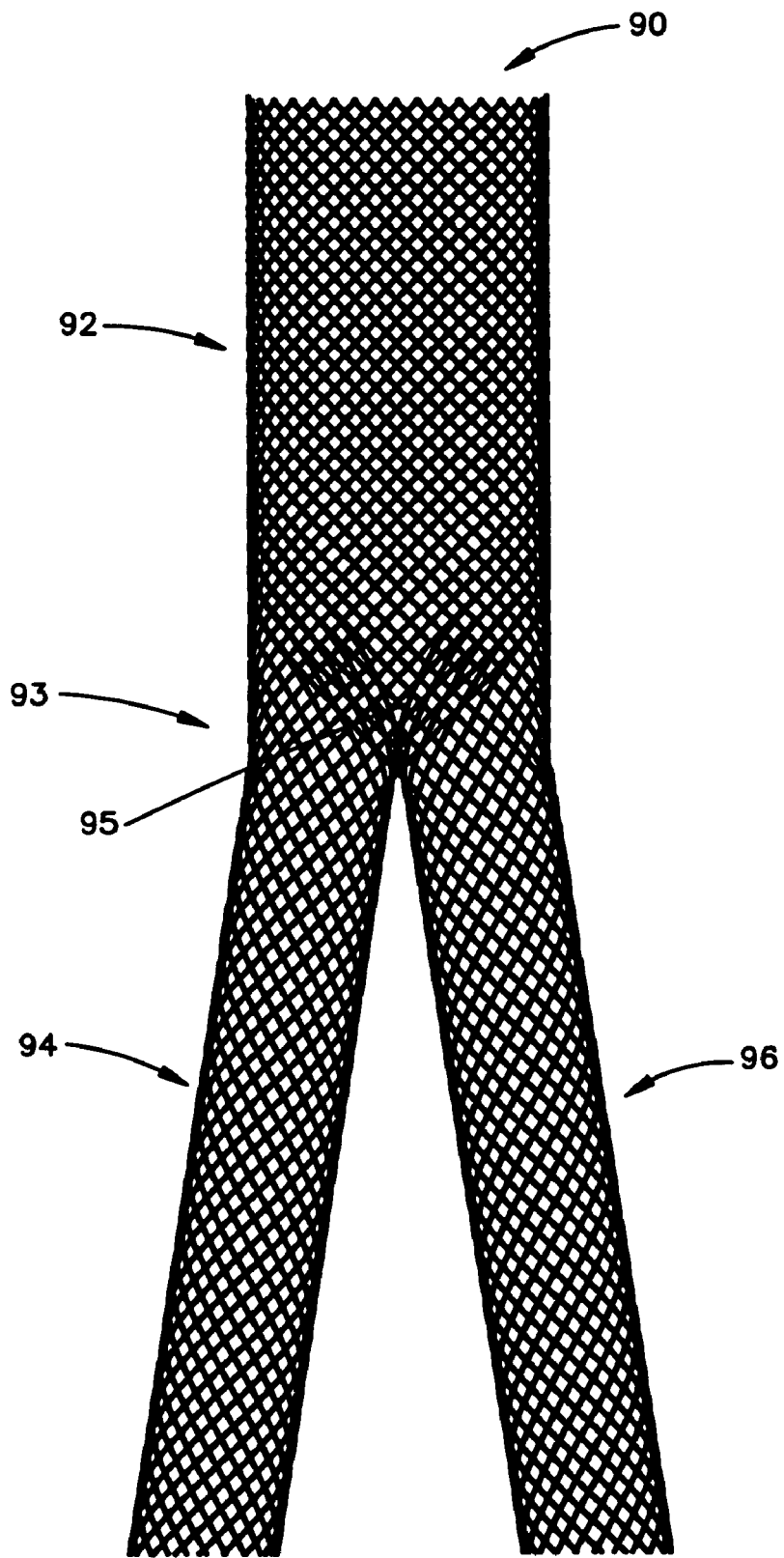
FIG. 2 shows an example of a bifurcation stent.

FIG. 2 shows an example of another medical device that is suitable for the present invention. In particular, this figure shows an example of a bifurcation stent 90, such as one that is suitable for treating abdominal aortic aneuryms. FIG. 2 is a view of a bifurcation stent 90 consisting of a trunk 92, a first illiac leg 94, and a second illiac leg 96, that both stem from the bifurcation region of the stent 93 and are separated at the ostium 95. The stent struts on the second illiac leg 96 of the stent make up the petal region.

Figure 3:
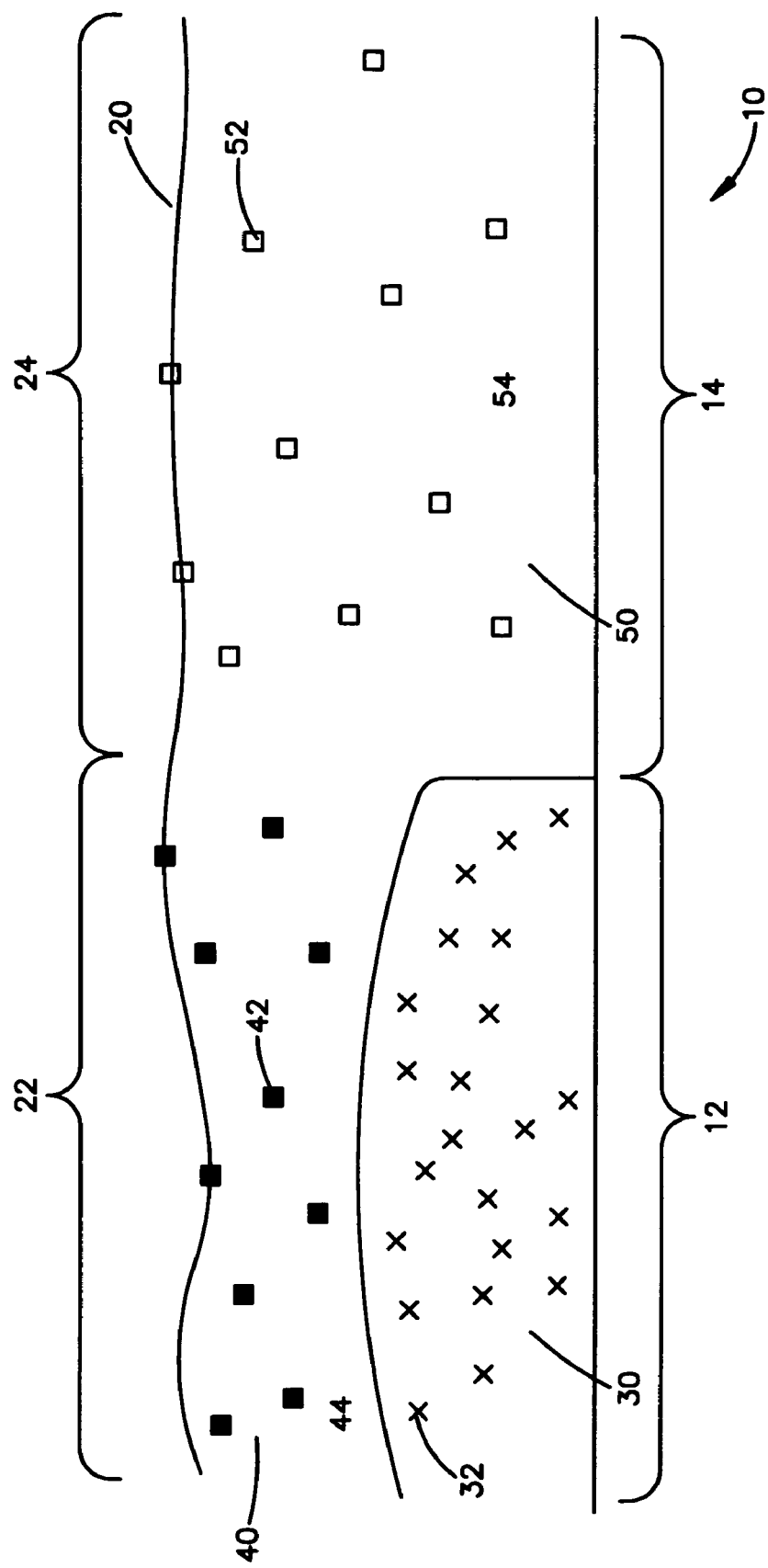
FIG. 3 is a cross-sectional view of a coating having a region containing an adhesion promoter and a contiguous region that is substantially free of any adhesion promoter.

FIG. 3 shows an embodiment of the present invention. More specifically, FIG. 3 is a cross-sectional view of a part of a medical device 10. The medical device, has a first region 12 and a second region 14. A coating 20 having a first coating region 22 and a second coating region 24 is disposed on the medical device. In particular, a first coating region 22 is disposed on the first region of the medical device 12, and a second coating region 24 is disposed on a second region of the medical device 14. For example, the first region of the medical device 12 can be an end portion of a stent and the second region of the medical device 14 can be the middle portion of the stent. Alternatively, the first region can be the middle portion of a stent and the second region can be an end portion. In FIG. 3 the first and second coating regions 22, 24 are contiguous or in contact with each other. In alternative embodiments, the first and second coating regions 22, 24 may be separated or spaced apart. In preferred embodiments the first and second coating regions conform to the sidewall stent structure so as to preserve the openings therein.

The first coating region 22 comprises a first coating composition 30, which can form a layer. The first coating composition 30 comprises an adhesion promoter 32. Furthermore, the first coating composition 30 in some embodiments can include a therapeutic agent and/or a polymer.

In the embodiment shown in FIG. 3, the first coating region 22 also includes a second coating composition 40, which is disposed on the first coating composition 30. The second coating composition 40 can form a layer. Also, the second coating composition 40 comprises a first therapeutic agent 42 and can also include a polymer 44. In certain embodiments, if there is a polymer in the first coating composition it can be the same or different from the polymer 44 of the second coating composition 40. In embodiments not shown, the second coating composition 40 can include an adhesion promoter. In alternative embodiments not shown, the first coating region 22 can include more than two coating compositions comprising an adhesion promoter, a polymer, and/or a therapeutic agent. The first coating region 22 can have more than two layers comprising combinations of adhesion promoters, polymers, and/or therapeutic agents that are identical or different.

The second coating region 24 comprises a third coating composition 50, which may form a layer. The third coating composition 50 comprises a second therapeutic agent 52, which may be the same as the first therapeutic agent 42 of the second coating composition 40. In certain embodiments, the second therapeutic agent 52 of the third coating composition 50 is different from the first therapeutic agent 42 of the second coating composition 40. The third coating composition 50 can also include a polymer 54, which can be the same as or different from the polymer in the first composition 30 or the polymer 44 in the second composition 40. In some embodiments, the third coating composition 50 of the second coating region 24 is substantially free of the adhesion promoter 32 or any adhesion promoter, i.e. contains less than 1% by weight of an adhesion promoter, or is free of any adhesion promoter. In other embodiments, the third coating composition 50 can contain the same or a different adhesion promoter than used in the first coating composition 30. Also, the second and third coating composition can be the same, i.e. contain the same constituents in the same amounts. In certain embodiments not shown, the second coating region 24 can include more than one coating composition comprising an adhesion promoter, a polymer and/or a therapeutic agent. The second coating region 24 can have layers comprising combinations of adhesion promoters, polymers, and/or therapeutic agents that are identical or different. The one or more coating compositions in the first coating region 22 and the second coating region 24 can be identical or different.

Since the inclusion of an adhesion promoter in a coating region generally reduces the release of a therapeutic agent from that coating region, a coating region containing an adhesion promoter can be disposed at specific locations on a medical device where reduced release of the therapeutic agent is desired. For example, the first coating region can be disposed on an end portion of a stent, where reduced release may be desired, and the second coating region can be disposed on the middle portion of the stent. In one embodiment, the adhesion promoter reduces the rate of release of the first therapeutic agent from the first coating region such that the rate of release of the first therapeutic agent from the first coating region is less that the rate of release of the second therapeutic agent from the second coating region.

Also, when the medical device is a stent, such as an intravascular stent, that has a sidewall stent structure with openings therein, in certain embodiments, the first and/or second coating regions conform to the sidewall stent structure so as to preserve the openings therein.

Figure 4A:
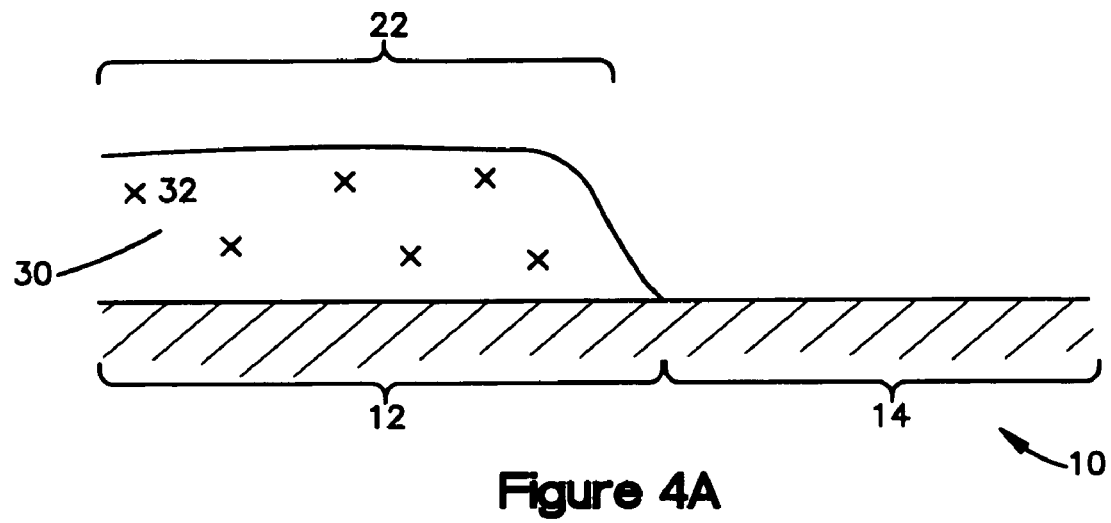
FIGS. 4A-4B shows a method for making the coating of FIG. 3.
Figure 4B:
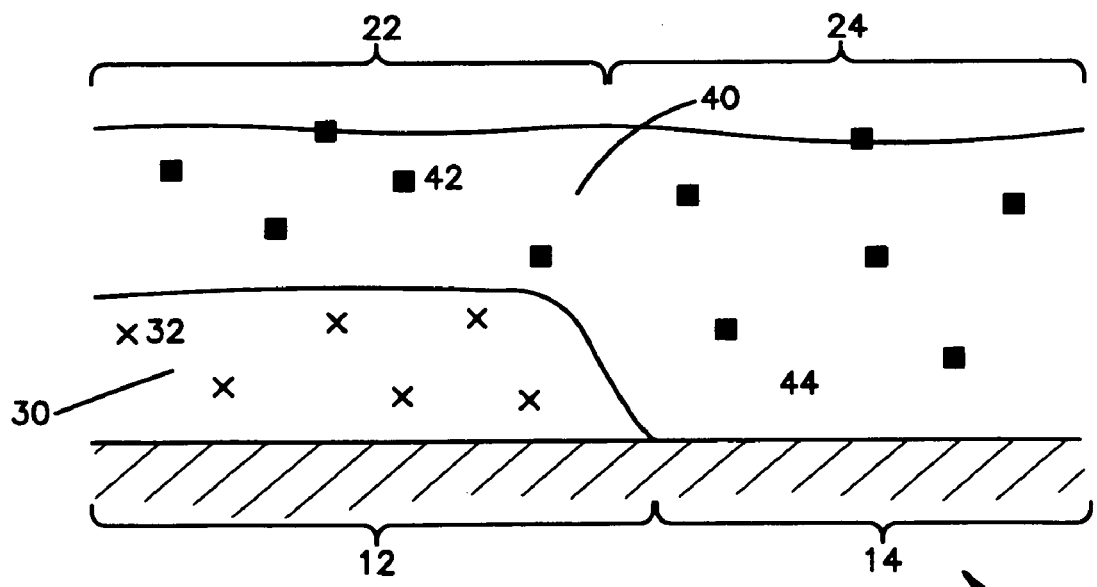

FIGS. 4A and 4B illustrates an exemplary method of making the coated medical device of the present invention. FIG. 4A shows a first region 12 and a second region 14 of a medical device 10. A first coating composition 30 is disposed on the first region 12 to form part of a first coating region 22. The first coating composition 30 comprises an adhesion promoter 32. FIG. 4B shows a subsequent step in the method. A second coating composition 40 disposed on the first coating composition 30 to form a first coating region 22 disposed on the first region 12. In this embodiment, the second coating composition 40 is the same as the coating composition used to form a second coating region 24. In other words, the second coating composition 40 is also used to form the second coating region 24. The second coating composition 40 comprises a therapeutic agent 42 and an polymer 44. This second coating composition 40 can be applied to the first coating composition 30 before the second coating composition 40 is used to form the second coating region 24 or vice versa.

The coating compositions can be applied by any method to the medical device. Examples of suitable methods include, but are not limited to, spraying such as by conventional nozzle or ultrasonic nozzle, dipping, rolling, electrostatic deposition, ink-jet coating and a batch process such as air suspension, pan-coating or ultrasonic mist spraying. Also, more than one coating method can be used to apply a coating composition onto the medical device.

The coating compositions are formed by combining the constituents of the composition, e.g. adhesion promoter, polymer and/or therapeutic agent. Solvents that may be used to prepare the coating compositions, particularly ones that include a polymer. Examples of suitable solvents include, but are not limited to, tetrahydrofuran, methylethylketone, chloroform, toluene, acetone, isooctane, 1,1,1 trichloroethane, dichloromethane, isopropanol, IPA, and mixture thereof.

Figure 5A:
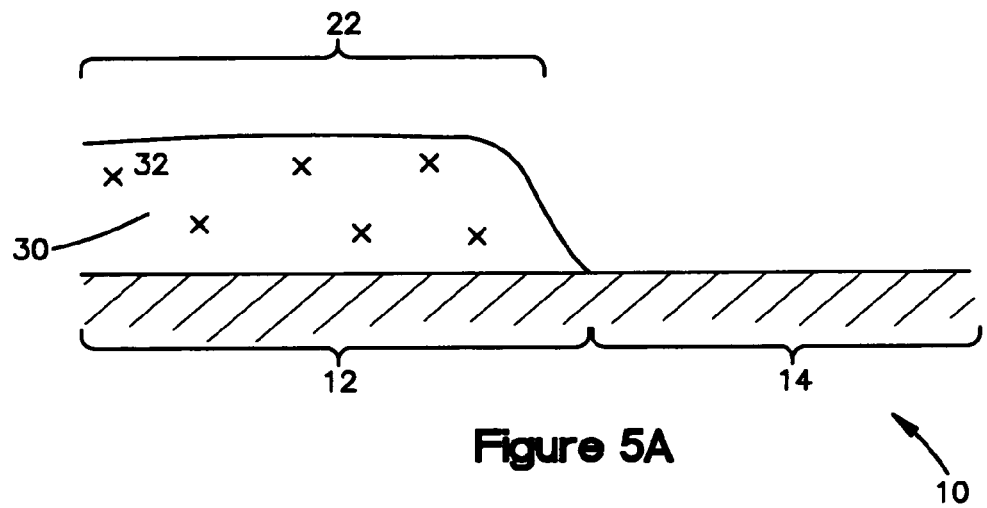
FIGS. 5A-5D shows other methods for making the coatings of the present invention.

FIGS. 5A-5D show other embodiments for making the coated medical device of the present invention. FIG. 5A shows a first region 12 and a second region 14 of a medical device 10. A first coating composition 30 is disposed on the first region 12 to form part of a first coating region 22. The first coating composition 30 comprises an adhesion promoter 32.

Figure 5B:
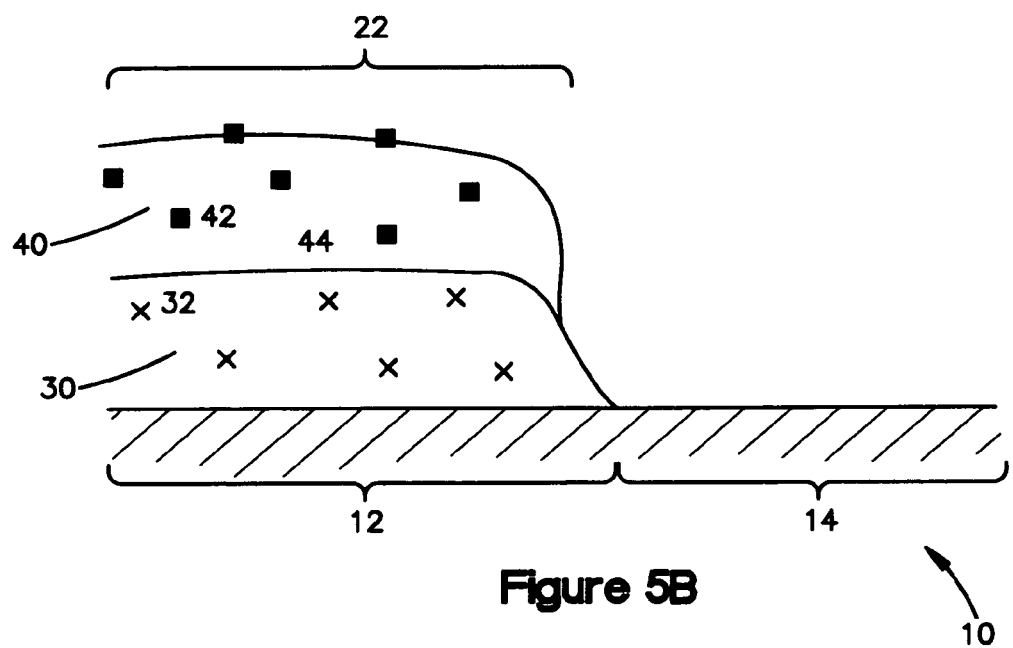

FIG. 5B shows a subsequent step in the method. In this figure, a second coating composition 40 is disposed on the first coating composition 30 disposed on the first region of a medical device 12. The second coating composition 40 comprises a therapeutic agent 42 and a polymer 44. If a polymer is used in the first coating composition 30, it can be the same as or different from the polymer 44 of the second coating composition 40.

Figure 5C:
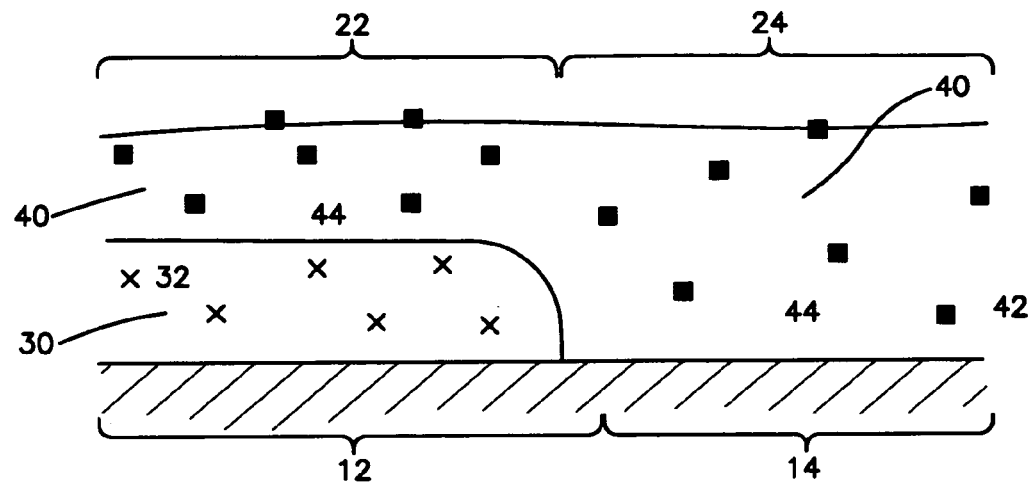

FIG. 5C shows the next step in the method. In this embodiment, the second coating composition 40, which was disposed on the first coating composition 30, is disposed on the second region 14 of the medical device 10 to form the second coating region 24. Although FIGS. 5B-5C shows that the second coating composition 40 is disposed over the first coating composition 30 before it is used to form the second coating region 24, the second coating composition 40 can be used to form the second coating region 24 before it is disposed on the first coating composition 30.

Figure 5D:
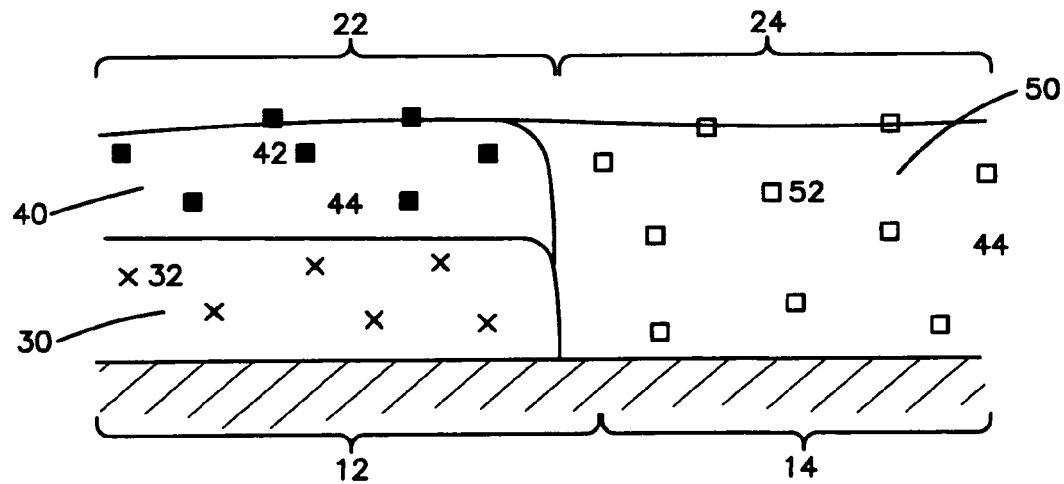

FIG. 5D shows an alternative to the step shown in FIG. 5C. This figure shows an embodiment where a third coating composition 50 used to form the second coating region 24 is different from the second coating composition 40. The third coating composition 50 may form a layer. Also, the third coating composition 50 comprises a second therapeutic agent 52, which may be the same as the first therapeutic agent 42 of the second coating composition 40. In certain embodiments, the second therapeutic agent 52 of the third coating composition 50 is different from the first therapeutic agent 42 of the second coating composition 40. The third coating composition 50 can include a polymer 44. The polymer 44 of the third coating composition 50 can be the same as or different from the polymer(s) of the first or second coating compositions. In some embodiments, the third coating composition 50 is substantially free of the adhesion promoter or any adhesion promoter, i.e. contains less than 1% by weight of an adhesion promoter, or is free of any adhesion promoter.

Figure 6:
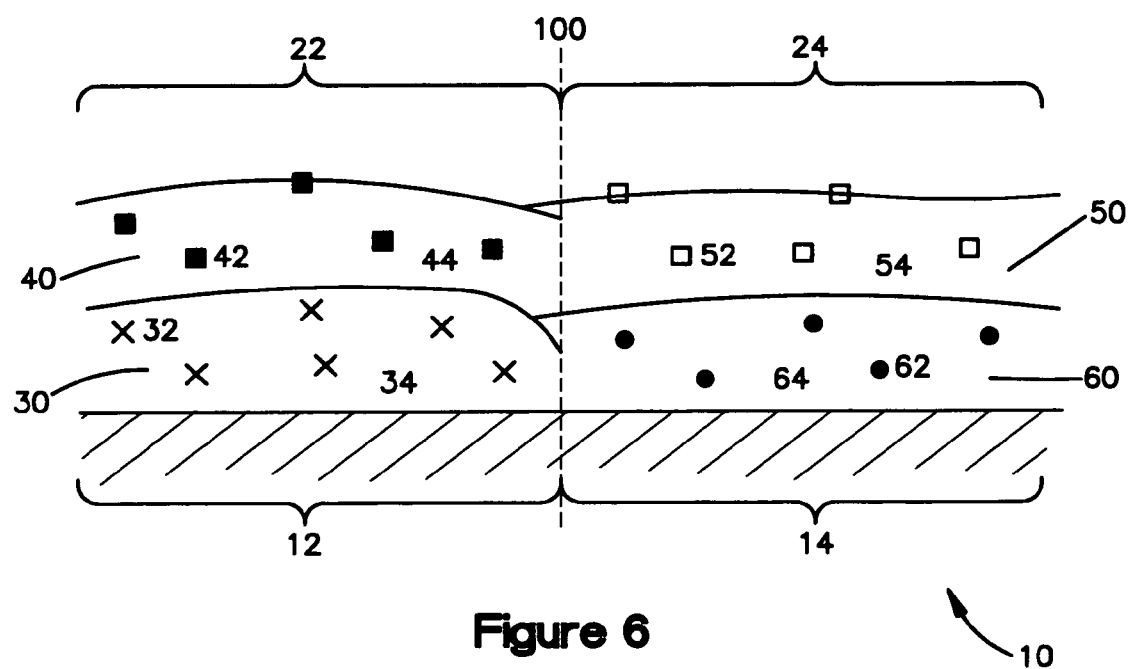
FIG. 6 shows an embodiment of a coating of the present invention where two contiguous regions of the coating each contain an adhesion promoter.

FIG. 6 shows yet another embodiment of a coated medical devices of the present invention. In FIG. 6 a medical device 10 comprises a first region 12 and a second region 14. A first coating region 22 comprises a first coating composition 30, which can form a layer. The first coating composition 30 comprises an adhesion promoter 32 and in certain embodiments, such as the one depicted, a first polymer 34. Furthermore, the first coating composition in some embodiments can include a therapeutic agent.

In this embodiment, the first coating region 22 also includes a second coating composition 40, which is disposed on the first coating composition 30. The second coating composition 40 can form a layer. Also, the second coating composition 40 comprises a first therapeutic agent 42 and can also include a second polymer 44. In certain embodiments, the first polymer 34 of the first coating composition 30 can be the same as the second polymer 44 of the second coating composition 40. In other embodiments, the first polymer 34 of the first coating composition 30 can be different from the second polymer 44 of the second coating composition 40. In some embodiments, the second coating composition 40 can also include an adhesion promoter which is the same as or different from the adhesion promoter 32 in the first coating composition 30.

The coating also comprises a second coating region 24. In an alternative embodiment, the first and second coating regions 22, 24 may be separated or spaced apart. In this embodiment, the second coating region 24 comprises a third coating composition 50, which may form a layer, disposed over a fourth coating composition 60. The third coating composition 50 comprises a second therapeutic agent 52, which may be the same as the first therapeutic agent 42 of the second coating composition 40. The third coating composition 50 can also include a third polymer 54, which can be the same as the first polymer 34 or the second polymer 44. In some embodiments, the third coating composition 50 or the second coating region 24 is substantially free of any adhesion promoter, i.e. contains less than 1% by weight of the adhesion promoter or any adhesion promoter, or is free of any adhesion promoter. Also, the second coating composition 40 and third coating composition 50 can be the same, i.e. contain the same constitutes in the same amounts.

The fourth coating composition 60 may form a layer. In some instances, the fourth coating composition 60 forms a first layer and the third coating composition 50 forms a second layer disposed over the first layer. The fourth coating composition 60 comprises a second adhesion promoter 62, which may be the same as or different from the first adhesion promoter 32 of the first coating composition 30. Also, the fourth coating composition 60 can include a fourth polymer 64, which can be the same as the first polymer 34 or the second polymer 44 or the third polymer 54. In some embodiments, the fourth coating composition 60 is substantially free of any adhesion promoter, i.e. contains less than 1% by weight of the adhesion promoter or any adhesion promoter, or is free of any adhesion promoter.

Figure 7:
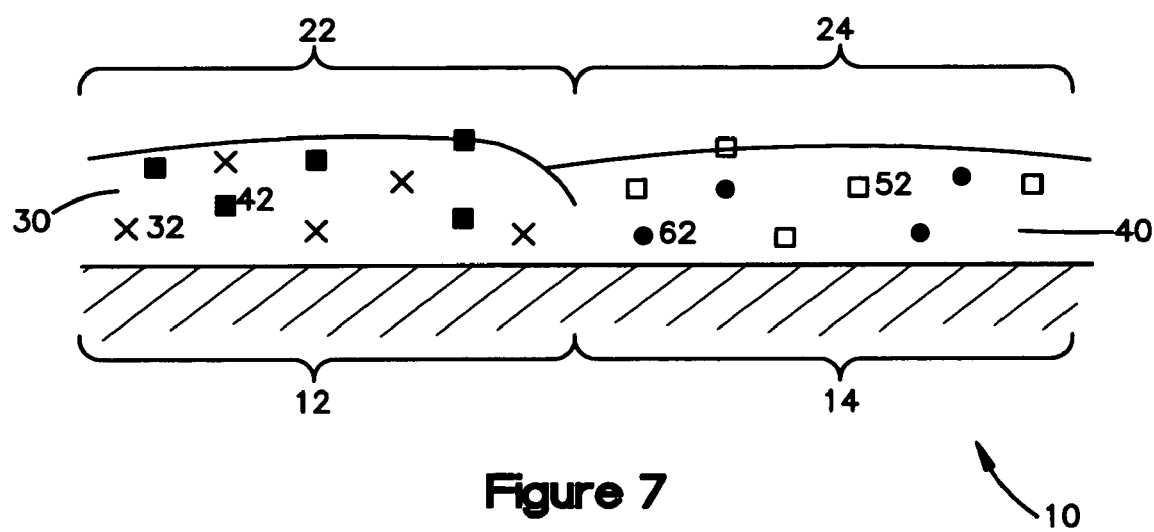
FIG. 7 shows another embodiment of the coating of the present invention where two contiguous regions of the coating each contain an adhesion promoter.

FIG. 7 shows another embodiment of coated medical device of the present invention. In FIG. 7 a medical device 10 comprises a first region 12 and a second region 14. A first coating region 22 comprises a first coating composition 30, which can form a layer. The first coating composition 30 comprises an adhesion promoter 32 and optionally a first polymer, and a first therapeutic agent 42. Furthermore, the first coating region 22 can include one or more additional layers of coating compositions with either adhesion promoters, polymers, and/or therapeutic agents.

The second coating region 24 of the coating comprises a second coating composition 40, which may form a layer. The second coating composition 40 comprises a second adhesion promoter 52, which may be the same as the first adhesion promoter 32 of the first coating composition 30. The second coating composition 40 can include a second therapeutic agent 62, which may be the same as or different from the first therapeutic agent 42. The second coating composition 40 can also include a polymer, which can be the same as the polymer in the first composition. Furthermore, the second coating region can include one or more additional layers of coating compositions with either adhesion promoters, polymers, and/or therapeutic agents.

A. Medical Devices

The coated medical devices of the present invention can be inserted and implanted in the body of a patient. Medical devices suitable for the present invention include, but are not limited to, stents, surgical staples, catheters, such as balloon catheters, central venous catheters, and arterial catheters, guidewires, cannulas, cardiac pacemaker leads or lead tips, cardiac defibrillator leads or lead tips, implantable vascular access ports, blood storage bags, blood tubing, vascular or other grafts, intra aortic balloon pumps, heart valves, cardiovascular sutures, total artificial hearts and ventricular assist pumps, and extra corporeal devices such as blood oxygenators, blood filters, septal defect devices, hemodialysis units, hemoperfusion units and plasmapheresis units.

Medical devices suitable for the present invention include those that have a tubular or cylindrical like portion. The tubular portion of the medical device need not be completely cylindrical. For instance, the cross section of the tubular portion can be any shape, such as rectangle, a triangle, etc., not just a circle. Such devices include, without limitation, stents, balloon catheters, and grafts. A bifurcation stent is also included among the medical devices which can be fabricated by the method of the present invention.

Medical devices that are particularly suitable for the present invention include any kind of stent for medical purposes which is known to the skilled artisan. Preferably, the stents are intravascular stents that are designed for permanent implantation in a blood vessel of a patient and that have a sidewall stent structure having openings therein. Suitable intravascular stents include self expanding stents and balloon expandable stents. Examples of self expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon expandable stents are shown in U.S. Pat. No. 5,449,373 issued to Pinchasik et al. In preferred embodiments, the stent suitable for the present invention is an Express stent. More preferably, the Express stent is an Express™ stent or an Express2™ stent (Boston Scientific, Inc. Natick, Mass.).

Medical devices that are suitable for the present invention may be fabricated from metallic, ceramic, or polymeric materials, or a combination thereof. Preferably, the materials are biocompatible. Metallic material is more preferable. Suitable metallic materials include metals and alloys based on titanium (such as nitinol, nickel titanium alloys, thermo memory alloy materials), stainless steel, tantalum, nickel chrome, or certain cobalt alloys including cobalt chromium nickel alloys such as Elgiloy® and Phynox®. Metallic materials also include clad composite filaments, such as those disclosed in WO 94/16646.

Suitable ceramic materials include, but are not limited to, oxides, carbides, or nitrides of the transition elements such as titanium oxides, hafnium oxides, iridiumoxides, chromium oxides, aluminum oxides, and zirconiumoxides. Silicon based materials, such as silica, may also be used. The polymeric material may be biostable. Also, the polymeric material may be biodegradable. Suitable polymeric materials include, but are not limited to, styrene isobutylene styrene, polyetheroxides, polyvinyl alcohol, polyglycolic acid, polylactic acid, polyamides, poly-2-hydroxy-butyrate, polycaprolactone, poly(lactic-co-clycolic)acid, and Teflon.

Polymeric materials may be used for forming the medical device in the present invention include without limitation isobutylene-based polymers, polystyrene-based polymers, polyacrylates, and polyacrylate derivatives, vinyl acetate-based polymers and its copolymers, polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for medical devices include without limitation dacron polyester, poly (ethylene terephthalate), polycarbonate, polymethylmethacrylate, polypropylene, polyalkylene oxalates, polyvinylchloride, polyurethanes, polysiloxanes, nylons, poly (dimethyl siloxane), polycyanoacrylates, polyphosphazenes, poly(amino acids), ethylene glycol I dimethacrylate, poly (methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(γ-caprolactone), poly(γ-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Medical devices may also be made with non-polymeric materials. Examples of useful non-polymeric materials include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

B. Therapeutic Agents

The term "therapeutic agent" as used in the present invention encompasses drugs, genetic materials, and biological materials and can be used interchangeably with "biologically active material". In one embodiment, the therapeutic agent is an anti-restenotic agent. In other embodiments, the therapeutic agent inhibits smooth muscle cell proliferation, contraction, migration or hyperactivity. Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), pimecrolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, antiplatelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, paclitaxel (as well as its derivatives, analogs or paclitaxel bound to proteins, e.g. Abraxane™) 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, or its analogs or derivatives. In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;

anti-inflammatory agents such as glucocorticoids, betamethasone, dexamethasone, prednisolone, corticosterone, budesonide, estrogen, sulfasalazine, rosiglitazone, mycophenolic acid and mesalamine;

anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives;

anesthetic agents such as lidocaine, bupivacaine, and ropivacaine;

anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endothelial growth factors (VEGF, all types including VEGF-2), growth factor receptors, transcriptional activators, and translational promoters;

vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents, vasodilating agents, and agents which interfere with endogenous vasoactive mechanisms;

anti-oxidants, such as probucol;

antibiotic agents, such as penicillin, cefoxitin, oxacillin, tobranycin, rapamycin (sirolimus);

angiogenic substances, such as acidic and basic fibroblast growth factors, estrogen including estradiol (E2), estriol (E3) and 17-beta estradiol;

drugs for heart failure, such as digoxin, beta-blockers, angiotensin-converting enzyme (ACE) inhibitors including captopril and enalopril, statins and related compounds; and macrolides such as sirolimus or everolimus.

Preferred biological materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other suitable therapeutic agents include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

Other preferred therapeutic agents include nitroglycerin, nitrous oxides, nitric oxides, aspirins, digitalis, estrogen derivatives such as estradiol and glycosides.

In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration.

In certain embodiments, the therapeutic agents for use in the medical devices of the present invention can be synthesized by methods well known to one skilled in the art. Alternatively, the therapeutic agents can be purchased from chemical and pharmaceutical companies.

In some embodiments, the therapeutic agent comprises at least 5%, at least 10%, at least 20%, at least 30%, at least 40%, at least 50%, at least 60%, at least 70%, at least 80%, at least 90%, at least 95%, at least 97%, at least 99% or more by weight of the coating composition. Preferably, the therapeutic agent is about 0.01 to about 60 percent by weight of the coating composition that contains the therapeutic agent. More preferably, the therapeutic agent is about 5 to about 60 percent by weight of the coating composition that contains the therapeutic agent.

C. Suitable Polymers

Polymers useful for forming the coating compositions should be ones that are biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. The polymer is selected to allow the coating to better adhere to the surface of the strut when the stent is subjected to forces or stress. Furthermore, although the coating can be formed by using a single type of polymer, various combinations of polymers can be employed.

Generally, when a hydrophilic therapeutic agent is used then a hydrophilic polymer having a greater affinity for the therapeutic agent than another material that is less hydrophilic is preferred. When a hydrophobictherapeutic agent is used then a hydrophobic polymer having a greater affinity for the therapeutic agent is preferred.

Examples of suitable hydrophobic polymers or monomers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly(vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by Ra SiO 4-a/2, where R is a monovalent substituted or unsubstituted hydrocarbon radical and the value of a is 1 or 2; and naturally occurring hydrophobic polymers such as rubber.

Examples of suitable hydrophilic polymers or monomers include, but not limited to; (meth)acrylic acid, or alkaline metal or ammonium salts thereof; (meth)acrylamide; (meth) acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl (meth)acrylate and 2-hydroxypropyl (meth)acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl ($-SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

D. Adhesion Promoters

Materials that can be used as adhesion promoters in the present invention include those that are capable of reducing the release rate of a therapeutic agent from a coating as compared to the release of that therapeutic agent absent the adhesion promoter, including but not limited to copolymers of styrene and ethylene/butylene, iridium oxide and sulfonated styrene isobutylene copolymers.

In specific embodiments, the adhesion promoter comprises at least 5%, at least 10%, at least 20%, at least 30%, at least 40%, at least 50%, at least 60%, at least 70%, at least 80%, at least 90%, at least 95%, at least 97%, at least 99% or more by weight of the coating composition that contains the adhesion promoter. Preferably, the adhesion promoter is less than about 10 percent by weight of the coating composition that contains the adhesion promoter. More preferably, the adhesion promoter is about 1 to about 5 percent by weight of the coating composition that contains the adhesion promoter. In some embodiments the weight percent of the adhesion promoter will be different between the different coating compositions. In specific embodiments, the weight percent of the adhesion promoter will be different between the different coating regions.

Coating compositions can be applied by any method to a surface of a medical device. Examples of suitable methods include, but are not limited to, spraying such as by conventional nozzle or ultrasonic nozzle, dipping, rolling, electrostatic deposition, and a batch process such as air suspension, pan coating or ultrasonic mist spraying. Also, more than one coating method can be used to make a medical device.

To facilitate application of the coating compositions, the constituents of the coating composition can be dissolved or suspended in a solvent. After application to the medical device, the solvent is removed, e.g. evaporated.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. and not for purposes of limitation. Changes and modifications may be made to the embodiments of the description and still be within the scope of the invention. Furthermore, obvious changes, modifications or variations will occur to those skilled in the art. Also, all references cited above are incorporated herein by reference, in their entirety, for all purposes related to this disclosure.

What is claimed is:

1. An implantable stent comprising
   (a) an intravascular sidewall stent structure having openings therein and designed for permanent implantation into a blood vessel of a patient; and
   (b) a coating disposed on the stent structure having
      (1) a first coating region disposed on a first region of the stent structure, wherein the first coating region comprises a first coating composition comprising a first adhesion promoter and a second coating composition comprising a first therapeutic agent disposed upon the first coating composition; and
      (2) a second coating region disposed on a second region of the stent structure, wherein the second coating region comprises a third coating composition comprising a second therapeutic agent and a second adhesion promoter different in composition from the first adhesion promoter, wherein the first adhesion promoter is selected from the group consisting of copolymers of styrene and ethylene/butylenes, iridium oxide, and sulfonated styrene isobutylene.

2. The stent of claim 1, wherein the first adhesion promoter reduces the rate of release of the first therapeutic agent from the first coating region such that the rate of release of the first therapeutic agent from the first coating region is less than the rate of release of the second therapeutic agent from the second coating region.

3. The stent of claim 1, wherein the first and second coating regions conform to the stent structure so as to preserve the openings of the stent structure.

4. The stent of claim 1, wherein the first coating region is contiguous with the second coating region.

5. The stent of claim 1, wherein the first adhesion promoter is less than about 10 weight percent of the first coating composition.

6. The stent of claim 1, wherein the first or the second therapeutic agent comprises paclitaxel.

7. The stent of claim 1, wherein the first or the second therapeutic agent comprises an antibiotic.

8. The stent of claim 1, wherein the first or the second therapeutic agent comprises rapamycin, everolimus, tacrolimus or pimecrolimus.

9. The stent of claim 1, wherein the first or the second therapeutic agent comprises an anti-restenotic agent.

10. The stent of claim 1, wherein the first or the second therapeutic agent inhibits smooth muscle cell proliferation, contraction, migration or hyperactivity.

11. The stent of claim 1, wherein the second or third coating composition comprises a polymer.

12. The stent of claim 1, wherein the stent structure comprises two end portions and a middle portion disposed between the two end portions, and wherein the first region of the stent structure is an end portion and the second region of the stent structure is a middle portion.

13. The stent of claim 1, wherein the stent is a bifurcation stent and wherein the second region of the stent structure is a region of the bifurcation stent that covers a side branch ostium.

14. The stent of claim 1, wherein the first and second regions are located on a common surface of the stent structure.

15. An implantable stent comprising
   (a) an intravascular sidewall stent structure having openings therein and designed for permanent implantation into a blood vessel of a patient; and
   (b) a coating disposed on the stent structure having
      (1) a first coating region disposed on a first region of the stent structure, wherein the first coating region comprises a first coating composition comprising an adhesion promoter and a second coating composition comprising a therapeutic agent disposed upon the first coating composition, wherein the adhesion promoter is selected from the group consisting of copolymers of styrene and ethylene/butylenes, iridium oxide, and sulfonated styrene isobutylene; and
      (2) a second coating region, which is contiguous with the first coating region, disposed on a second region of the stent structure, wherein the second coating region comprises the second coating composition, and wherein the second coating region is substantially free of any adhesion promoter.

16. An implantable stent comprising
   (a) an intravascular, metallic, balloon-expandable sidewall stent structure having openings therein and designed for permanent implantation into a blood vessel of a patient; and
   (b) a coating disposed on the stent structure having
      (1) a first coating region disposed on a first region of the stent structure, wherein the first coating region comprises a first coating composition comprising an adhesion promoter and a second coating composition comprising an anti-restenotic agent disposed upon the first coating composition, wherein the adhesion promoter is selected from the group consisting of copolymers of styrene and ethylene/butylenes, iridium oxide, and sulfonated styrene isobutylene; and
      (2) a second coating region, which is contiguous with the first coating region, disposed on a second region of the stent structure, wherein the second coating region comprises the second coating composition, and wherein the second coating region is substantially free of any adhesion promoter; and
   wherein the first and second coating regions conform to the openings of the sidewall stent structure so as to preserve the openings.

17. An implantable stent comprising
   (a) an intravascular sidewall stent structure with openings designed for permanent implantation into a blood vessel of a patient; and
   (b) a coating disposed on the stent structure having
      (1) a first coating region disposed on a first region of the stent structure, wherein the first coating region comprises a first coating composition comprising a first adhesion promoter and a second coating composition comprising a first therapeutic agent, the second coating composition being disposed on the first coating composition; and
      (2) a second coating region disposed on a second region of the stent structure, wherein the second coating region comprises a third coating composition comprising a second adhesion promoter different in composition from the first adhesion promoter and a fourth coating composition comprising a second therapeutic agent, the fourth coating composition being disposed on the fourth coating composition; and
   wherein the first adhesion promoter reduces the rate of release of the first therapeutic agent from the first coating region such that the rate of release of the first therapeutic agent from the first coating region is less than the rate of release of the second therapeutic agent from the second coating region; and
   wherein the stent structure comprises two end portions and a middle portion disposed between the two end portions, and wherein the first region of the stent structure is an end portion and the second region of the stent structure is the middle portion.

18. The stent of claim 17, wherein the first and second coating regions conform to the openings of the sidewall stent structure to preserve the openings.

19. The stent of claim 17, wherein the first coating region is contiguous with the second coating region.

20. The stent of claim 17, wherein the weight percent of the first adhesion promoter in the first coating composition is different from the weight percent of the second adhesion promoter in the third coating composition.

21. The stent of claim 17, wherein the first or the second therapeutic agent comprises paclitaxel.

22. The stent of claim 17, wherein the first or the second therapeutic agent comprises an antibiotic.

23. The stent of claim 17, wherein the first or the second therapeutic agent comprises rapamycin, everolimus, tacrolimus or pimecrolimus.

24. The stent of claim 17, wherein the first or the second therapeutic agent comprises an anti-restenotic agent.

25. The stent of claim 17, wherein the first or the second therapeutic agent inhibits smooth muscle cell proliferation, contraction, migration or hyperactivity.

26. The stent of claim 17, wherein the stent is a bifurcation stent and wherein the second region of the stent structure is a region of the bifurcation stent that covers a side branch ostium.

27. An implantable stent comprising
   (a) an intravascular, metallic, balloon-expandable stent sidewall structure having openings therein and designed for permanent implantation into a blood vessel of a patient; and
   (b) a coating disposed on the stent structure having
      (1) a first coating region disposed on a first region of the stent structure, wherein the first coating region comprises a first coating composition comprising a first adhesion promoter and a second coating composition comprising an anti-restenotic agent, the second coating composition being disposed on the first coating composition; and
      (2) a second coating region disposed on a second region of the stent structure, wherein the second coating region comprises a third coating composition comprising a second adhesion promoter different in composition from the first adhesion promoter and a fourth coating composition comprising the anti-restenotic agent the fourth coating composition being disposed on the third coating composition; and wherein the first adhesion promoter reduces the rate of release of the anti-restenotic agent from the first coating region such that the rate of release of the anti-restenotic agent from the first coating region is less than the rate of release of the anti-restenotic agent from the second coating region; and wherein the first and second coating regions conform to the openings of the sidewall stent structure so as to preserve the openings.

* * * * *

UNITED STATES PATENT AND TRADEMARK OFFICE
CERTIFICATE OF CORRECTION

| | | Page 1 of 1 |
|---|---|---|
| PATENT NO. | : 7,879,086 B2 | |
| APPLICATION NO. | : 11/409468 | |
| DATED | : February 1, 2011 | |
| INVENTOR(S) | : Liza J. Davis | |

It is certified that error appears in the above-identified patent and that said Letters Patent is hereby corrected as shown below:

Col. 20, line 10, after "the", change "fourth" to --third--.

Signed and Sealed this
Twenty-seventh Day of September, 2011

David J. Kappos
*Director of the United States Patent and Trademark Office*